United States Patent [19]
Thibodaux

[11] Patent Number: 5,286,249
[45] Date of Patent: Feb. 15, 1994

[54] BRACE FOR FIXATION OF BONE FRACTURES

[76] Inventor: Peggy L. Thibodaux, P.O. Box 6685, Bakersfield, Calif. 93386-6685

[21] Appl. No.: 854,660
[22] PCT Filed: Oct. 31, 1989
[86] PCT No.: PCT/US89/04880
   § 371 Date: Apr. 29, 1992
   § 102(e) Date: Apr. 29, 1992
[51] Int. Cl.⁵ ............................................. A61F 5/00
[52] U.S. Cl. ...................................... 602/12; 602/5; 602/6; 602/20; 602/23; 606/54; 606/74
[58] Field of Search .................... 602/5, 6, 12, 14, 20, 602/21, 23; 606/53, 54, 74, 86

[56] References Cited

U.S. PATENT DOCUMENTS

| | | | |
|---|---|---|---|
| 323,775 | 8/1885 | Bender et al. | 602/12 |
| 1,233,112 | 7/1917 | Nylander | 602/12 |
| 2,318,864 | 5/1943 | Jackson | 602/21 |
| 3,710,789 | 1/1973 | Ersek | 606/74 X |
| 3,776,225 | 12/1973 | Lonardo | 602/21 |
| 3,850,167 | 11/1974 | Seeley | 602/6 |
| 3,955,565 | 5/1976 | Johnson, Jr. | 602/12 |
| 4,393,866 | 7/1983 | Finnieston | |
| 4,436,088 | 3/1984 | Finnieston | |
| 4,662,364 | 5/1987 | Viegas et al. | |
| 4,768,502 | 9/1988 | Lee | 602/6 |
| 4,796,611 | 1/1989 | Wardlaw | 602/12 |
| 5,171,310 | 12/1992 | Chisena | 602/20 X |

FOREIGN PATENT DOCUMENTS 3031021 4/1982 Fed. Rep. of Germany.

OTHER PUBLICATIONS

Zimmer Orthopedics sales literature entitled "External Fracture Fixation" (date unknown).
Zagorski, et al., "Diaphyseal Fractures of the Humerus", 70-A J. Bone Joint Surgery 607 (1988).
Galveston Manufacturing Co., Sales literature entitled "Galveston Metacarpal Brace ™" (publication date unknown, but after May of 1987).
Viegas, et al., "Functional Bracing of Fractures of the Second through Fifth Metacarpals", 12A J. Hand Surgery 139 (1987).
Naver, et al., "Humeral Shaft Fractures Treated with a Ready-Made Fracture Brace", 106 Arch. Orthop. Trauma Surg. 20 (1986).
Moss, et al. "Free Vascularized Fibular Graft to Reconstruct Early Traumatic Humeral Defect", 16 Injury: Brit. J. Accidental Surg. 41 (1984).
Epps, Jr. "Fractures of the Shaft of the Humerus", in C. A. Rockwood Jr., et al. (Eds.), Fractures in Adults, Philadelphia: J. B. Lippincott, pp. 653–674 (1984).
Balfour, et al., "Diaphyseal Fractures of the Humerus Treated with a Ready-Made Fracture Brace", 64-A J. Bone Joint Surgery 11 (1982).
Sarmiento, et al., "Functional Bracing of Fractures of the Shaft of the Humerus", 59-A, J. Bone Joint Surgery 596 (1977).
McMaster, et al., "Cast Brace for the Upper Extremity", 109 Clin. Orthopedics and Related Research 126 (1975).
Holm, "Management of Humeral Shaft Fractures", 71 Clin. Orthopedics and Related Research 132 (1970).
Kujat, et al., Funktionelle Frakturbehandlung im Brace, 107 Zentralblatt für Chirurgie 1417–1423 (1984).
Ricciardi-Pollini et al., The Treatment of Diaphyseal Fractures by Functional Bracing, 2nd Orthopaedic Clinic, University [La. Sapienza] Rome, 199–205 (date uncertain).

Primary Examiner—Richard J. Apley
Assistant Examiner—Linda C. M. Dvorak
Attorney, Agent, or Firm—Vaden, Eickenroht, Thompson, Boulware & Feather

[57] ABSTRACT

A brace for external fixation of long bone fractures which includes "I"-shaped member and cross-shaped elongate members, both of which are curved along a longitudinal axis to fit around the limb and which interlap to provide circumferential support. The two-piece, curved configuration concentrates the load applied to the limb over a smaller surface area and is, therefore, more effective at immobilizing the fractured bone while allowing access to the skin for wound management, surgery, and hygiene without removing the brace. The configuration also makes possible the adjustment of the brace at three independent points to provide for improved fit over a wider variety of sizes and shapes of limbs than previously available.

11 Claims, 2 Drawing Sheets

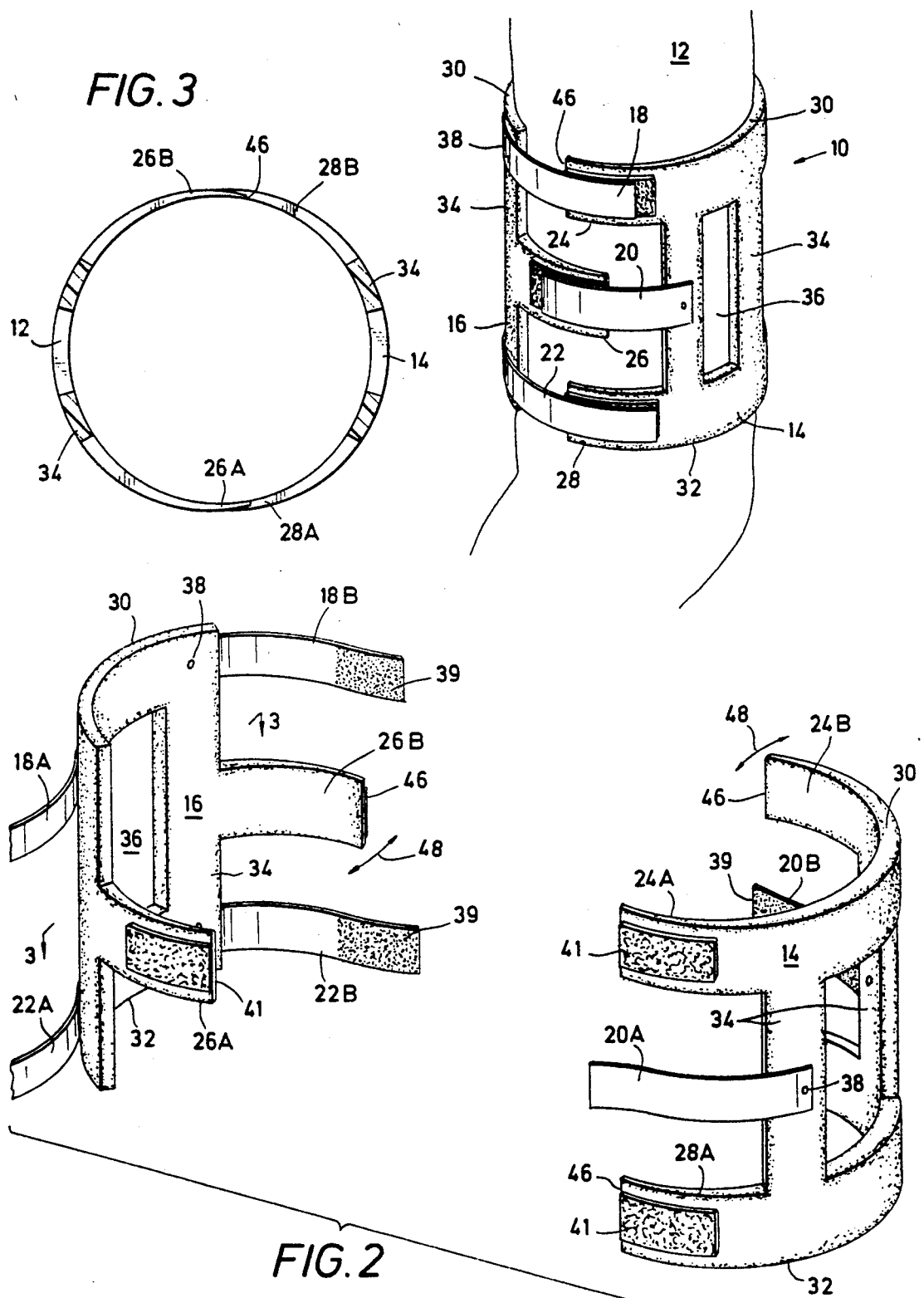

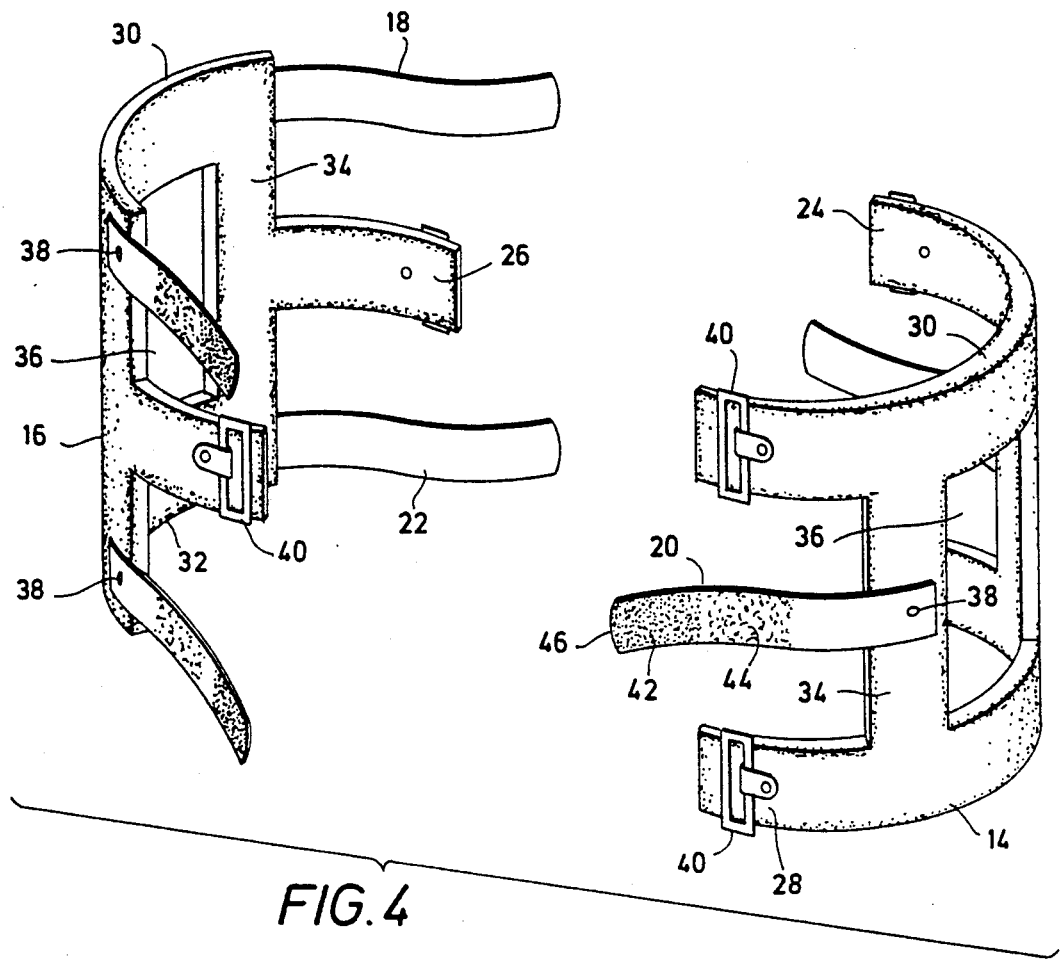
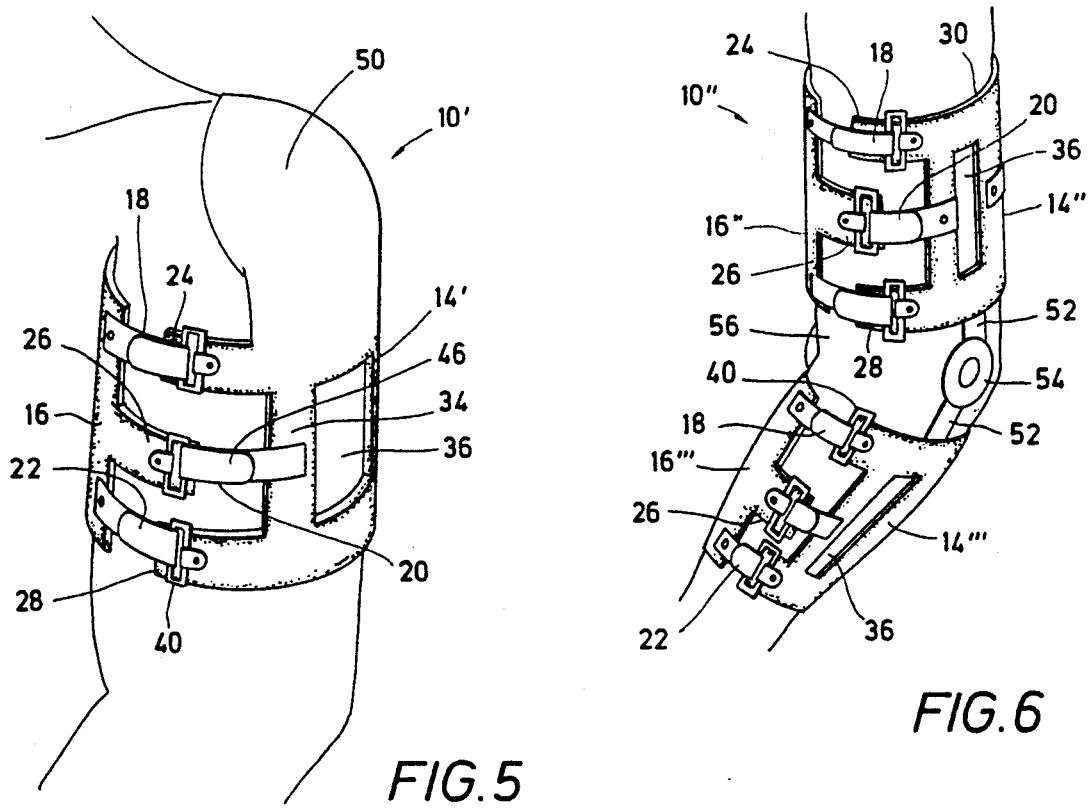
FIG. 4
FIG. 5
FIG. 6

BRACE FOR FIXATION OF BONE FRACTURES

BACKGROUND OF THE INVENTION

The present invention relates to a brace for external fixation of bone fractures. More particularly, the present invention relates to an apparatus for external fixation of a fracture of a long bone of a limb which is conveniently applied, allows access to a wound, and is comfortable to wear.

External fixation, or bracing, of fractures of the long bones of the body has become an increasingly common practice. The technique has become increasingly common as a result of the work conducted by Dr. Augusto Sarmiento beginning in about 1963 and published, for instance, at 59 J. Bone Joint Surg. [Am.] 596–601 (1977). The technique has been found especially useful for patients with markedly comminuted fractures, infected nonunion, bone defect or loss, extensive skin or soft tissue wounds in an open fracture, burn patients with fractures, aged patients in whom immobilization is undesirable, and in the case of a limb with concomitant fracture in the forearm or when early mobilization is indicated. Epps, C. H., Jr., Fractures of the Shaft of the Humerus, in Fractures in Adults, C. A. Rockwood, Jr. and D. P. Green, Eds., Philadelphia: J. B. Lippencott, pp. 653–674 (1984).

In spite of the proven utility of this technique, there is room for improvement in the apparatus used as the brace. The braces used for fixation of the humerus provide an example of how such braces can be improved. There are two basic types of braces available for external fixation of fractures of the humerus, the "clam shell" and so-called Sarmiento braces. The first is a hinged, cylindrical shell made of plastic with a soft liner. The Sarmiento brace is a cylindrical shell with a strap or cup over the shoulder to keep the brace from sliding down the arm. Neither allows air circulation and/or wound management and hygiene without removal. Both are problematical if the fracture is near the ends of the humerus. Further, neither is adjustable for patients with fat/muscle structures different from those of the idealized patients for whom these braces are made and supplied. For these, and other reasons, it is an object of the present invention to provide an improved brace for external fixation of long bone fractures.

Further prior art braces are shown in U.S. Pat. No. 4,436,088 and U.S. Pat. No. 4,393,866. The braces disclosed in these two U.S. specifications each consists of a principal elongate member of a substantially "U" cross section which carries straps and a second elongate member, also of substantially "U" cross section, adapted to be nested within the first member in an inverted orientation so that the two elongate members can be used to surround a limb. The two members may be urged together by tightening the straps of the first member around the second member. Each member is provided with a few small apertures therein to help the limb that is carrying the brace to "breathe".

SUMMARY OF THE INVENTION

According to this invention, there is provided a long bone brace for external fixation of fractures of the limbs comprising a first elongate, substantially rigid member, a second elongate, substantially rigid member and a plurality of straps wherein the first member has a cross-arm at each end thereof, the ends of the cross-arms being relatively flexible; said second member has a cross-arm located at about the midpoint of the length thereof, the ends of the cross-arm being relatively flexible; a strap is affixed to each end of said first member for at least partly encircling a limb having a fractured bone therein when said first member is applied to one side of the limb and for engaging the ends of said second member to hold said second member in place on the other side of the limb, and a strap is affixed to said second member at about the midpoint thereof for at least partly encircling the limb and for engaging said first member, said straps causing the ends of the cross-arms of the first and second members to bend to conform to the shape of the limb when tightened around the limb, thereby resisting relative movement above and below the fracture in all directions.

Because the cross-arms conform to the shape of the limb, the pressure exerted by the trace on the patient's limb is concentrated, to provide a firm secure fixation of the fracture with a smaller total applied load than that applied by the prior art braces discussed above.

Preferably the surfaces of the first and second members which contact the limb when said straps are tightened are provided with padding.

Preferably the first member and the second member are each comprised of a pair of spaced bars joined at the ends thereof, the opening between the bars allowing access to a wound without removing the brace from the limb.

This invention thus provides an apparatus for external fixation of a fracture of a long bone of a limb comprising first and second substantially rigid elongate members having straps affixed to each end at about the midpoint thereof for encircling the limb and holding the elongate members thereto when tightened, the straps at the ends of the elongate members being positioned above and below the fracture. The ends of the first elongate member and the approximate midpoint of the second elongate member are provided with flexible cross-arms which are bent by tightening the respective strap so as to be closely applied to the external surface of the limb, thereby cooperating with the straps to resist relative movement of the fractured bone above and below the fracture. In a preferred embodiment, the cross-arms at the midpoint and the cross-arms at the ends of the elongate members are of sufficient length to interlap.

BRIEF DESCRIPTION OF THE DRAWINGS

The invention will be described, by way of example only with reference to the drawings, in which:

FIG. 1 is a perspective view of a preferred embodiment of a brace worn on the upper arm of a patient, FIG. 2 is an enlarged, exploded perspective view of the brace of FIG. 1, FIG. 3 is a sectional view of the brace of FIG. 1 taken at the point designated by the line 3—3 in FIG. 2, FIG. 4 is an exploded, perspective view of another preferred embodiment of a brace constructed in accordance with the present invention, FIG. 5 is a perspective view of another preferred embodiment of a brace constructed in accordance with the present invention that has been modified by the addition of a shoulder cup for use in connection with a fracture near the proximal end of the humerus, and FIG. 6 is a perspective view of another preferred embodiment of a brace constructed in accordance with the present invention that is used either in connection with fractures of both the humerus and the radius or ulna or in connection with a fracture near the distal end of the humerus or the proximal end of the radius or ulna.

DESCRIPTION OF THE PREFERRED EMBODIMENTS

Throughout this specification, the phrase "long bone" is used to denote those bones of the skeletal system which are elongated in their general shape. Such bones, at least in humans, generally include the bones of the limbs, e.g., the arms and legs, and specifically, the femur, radius, ulna, humerus, tibia or fibula. The apparatus of the present invention is of particular utility for external fixation of fractures of the femur and humerus, both of which are long bones, but by that statement, it is not intended to so restrict the application of this apparatus.

FIG. 1 shows a presently preferred embodiment of the apparatus, indicated generally at reference numeral 10, on the upper arm of a patient, e.g., in use for external fixation of a fracture of the humerus of the patient. The apparatus 10 is comprised generally of first and second substantially rigid elongate members 14 and 16, respectively, straps 18, 20, and 22, and flexible cross-arms 24, 26, and 28. The top and bottom straps 18 and 22, respectively, are affixed to first and second elongate members 14 and 16 at the respective ends 30 and 32 thereof, and middle strap 20 is affixed at about the midpoint of first and second elongate members 14 and 16. The flexible cross-arms 24 and 28 are also located at the ends 30 and 32 of elongate members 14 and 16, cross-arm 26 being located at about the midpoint.

First and second elongate members 14 and 16 are comprised of a material which is substantially rigid in the direction parallel to the bone to be braced. As shown in the figures, each of elongate members 14 and 16 is preferably comprised of spaced bars 34 joined at the ends 30 and 32 to provide an opening 36 therebetween. As shown in FIGS. 2 and 4, the elongate members 14 and 16 are curved on an axis parallel to that of the long bone to be braced so as to allow a close fit to the limb when applied thereto. The bars 34 may be comprised of metal, rigid plastic, or other material which is padded at least on those surfaces which contact the limb when applied thereto.

For reasons explained further below, the presently preferred material for construction of elongate members 14 and 16 is plastic which is covered by a layer of closed cell foam padding (not shown). The foam padding is preferably a water based, modified vinyl nitrile foam 1 mm thick, applied to elongate members 14 and 16 by dipping, spraying, or adhering sheets of the foam to the elongate members 14 and 16. The foam padding may be covered (to allow passage of air and water vapor) with, for example, nitrogen-blown rubber. Other materials which are appropriate for use as the foam padding include cross-linked polyethylene and any of several commercially available ethylene-vinyl acetate copolymers. Depending upon the particular material utilized, the foam can also be applied to the elongate members 14 and 16 by molding (either poured or injected) the foam and then adhering the foam to the elongate members 14 and 16. Such materials are all radiolucent in character, allowing the limb to be x-rayed without removing the apparatus 10. The preferred plastic comprising elongate members 14 and 16 is injection moldable polypropylene.

The straps 18, 20, and 22 are riveted (the rivets are shown at reference numeral 38 in FIGS. 1, 2, and 4) or otherwise affixed to elongate members 14 and 16. As shown in FIG. 1, straps 18, 20, and 22 encircle the limb (the upper arm 12 in FIG. 1) of the patient and hold the first and second elongate members 14 and 16 securely thereto when tightened. The straps 18 and 22 are positioned above and below the fracture point in the bone of the limb when elongate members 14 and 16 are secured to the limb. As shown in FIG. 2, the straps 18 and 22 are provided with VELCRO TM hooks 39 and the ends 30 and 32 of second elongate member 14 are provided with a strap of VELCRO TM loops 41, just as the straps 20 are provided with hooks 39 and the approximate midpoint of first elongate member 16 is provided with loops 41, for securing the apparatus 10 to the limb of the patient as shown in FIG. 1. That same result is achieved by using the D-loops 40 affixed to the ends 30 and 32 of second elongate member 16 and the approximate midpoint of first elongate member 14 as shown in FIG. 4. The straps 18, 20, and 22 having the D-loops 40 thereon are provided with a strap of VELCRO TM hooks 42 at the respective ends thereof with loops 44 on the outside surface thereof for receiving the hooks 42 when the ends of the straps are looped through D-loops 40.

Flexible cross-arms 24 and 28 are, as described above, located at each end of the first elongate member 14 and flexible cross-arm 26 is located at about midpoint of second elongate member 16. Cross-arms 24, 26, and 28 are, as shown in FIG. 2, curved on the same axis as the curve of elongate members 14 and 16, e.g., the axis of the bone to be braced. However, the radius of that curve is larger than the radius of curvature of the elongate members 14 and 16 to allow the apparatus 10 to be used on limbs having an extremely wide range of sizes and shapes. Each of the cross-arms 24, 26, and 28 is bent by the tightening of the respective strap 18, 20, and 22 so as to be closely applied to the external surface of the limb, thereby cooperating with the straps 18, 20, and 22 to resist movement of the fractured bone above and below the fracture in all directions, e.g., to "fix" the bone externally of the limb. By conforming the cross-arms 24, 26, 28 to the shape of the limb, the load applied to the limb is concentrated over a smaller area that the load applied by known braces so that the load which is applied is more effective, allowing a decrease in the overall load that is used to accomplish the fixation of the bone.

As noted above, the elongate members 14 and 16 are preferably comprised of plastic which is rigid along the longitudinal axis thereof. When plastic is used as the material comprising members 14 and 16, the cross-arms 24, 26, and 28 are integral with respective members 14 and 16 and the longitudinal rigidity and radial flexibility described above is achieved by using plastic of different thicknesses as shown in FIGS. 2, 3, and 4. Although not shown, the same result can be achieved with integral, spaced metal bars 34 comprising first and second elongate members 14 and 16 having piano hinges between the elongate members 14 and 16 and the respective cross-arms 24, 26 and 28. When hinged in this fashion, it is not necessary that the cross-arms 24, 26, and 28 themselves be flexible; instead, the ends 46 of the respective cross-arms 24, 26, and 28 need only be able to rotate with respect to a point located on the arc representing the radius of curvature of first and second elongate members 14 and 16 to conform to the shape of the limb when the straps 18, 20, and 22 are tightened around the limb. In other words, the ends 46 of cross-arms 24, 26, and 28 move in the direction of the arrows 48 (see FIGS. 2 and 4) according to whether straps 18, 20, and 22 are tight or loose.

Although not required, it is preferred that the cross-arms 24, 26, and 28 be of sufficient length to interlap when apparatus 10 is applied to this limb. In other words, as shown in FIG. 1, it is preferred that the ends 46 of cross-arm 26 on second elongate member 16 extend into the space between the cross-arms 24 and 28 of the first elongate member 18. Because of this preferred configuration, first and second elongate members 14 and 16 can be viewed as being I-shaped and cross-shaped members, respectively. In that manner, movement of the fractured bone above and below the fracture is more effectively resisted in all directions.

As noted above, elongate members 14 and 16 are preferably comprised of a pair of spaced bars 34 joined at the ends 30 and 32 thereof. This configuration allows access to the limb through the opening 36 for hygiene, surgical intervention, or wound management without removing the apparatus 10 from the limb. The embodiments shown in FIGS. 5 and 6 are characterized by the same advantages, and have been modified for specific uses. For instance, first elongate member 14' has been provided with an integral shoulder cup 50, thereby adapting the apparatus 10' shown in FIG. 5 for use in connection with a fracture at the extreme proximal end of the humerus. Similarly, each of the elongate members 14", 14'" and 16'" of the apparatus 10" shown in FIG. 6 is provided with an integral extension 52 mounted to a hinge 54, the axis of hinge 54 concentric with the axis of the elbow 56. Modification of the apparatus 10 in the manner shown in FIG. 6 adapts the apparatus 10 for use in connection with a fracture at (1) the extreme distal end of the humerus, (2) the extreme proximal end of either the radius or ulna, or (3) both locations (1) and (2).

The preferred embodiments of this invention comprise braces which concentrate pressure exerted on the patient's limb to provide firmer, or more secure, fixation of the fracture with a smaller total applied load than that applied by known prior art braces. By using a brace as described above, it is possible to decrease the surface area covered by the brace to allow for wound management in the vicinity of the fracture, e.g., in the case of a compound fracture, without removal of the brace. Further, the preferred brace described above is comprised of waterproof materials so that hygiene can be maintained without removal of the brace from the patient.

One advantage of the braces described above is that they can be used to properly fix a fracture near the end of a long bone.

The preferred embodiment of this invention comprises a brace of one size which is easily adjustable for use on patients having a wide range of different body sizes and fat/muscle structures. The brace has multiple points of adjustment to further improve the fit of the brace regardless of the size of the patient.

The brace described above can also be quickly and conveniently applied and/or removed by the patient.

I claim:

1. A brace for external fixation of a fracture of a long bone comprising:
   a first elongate, substantially rigid member having a cross-arm extending outwardly from each side of said first elongate member at each end thereof, the ends of the cross-arms being relatively flexible;
   a second elongate, substantially rigid member having a cross-arm extending outwardly from each side of said second elongate member located at about the midpoint of the length thereof, the ends of the cross-arm being relatively flexible;
   a strap affixed to each end of said second member for at least partly encircling a limb having a fractured bone therein when said second member is applied to one side of the limb and for engaging the ends of said first member to hold said first member in place on the other side of the limb; and
   a strap affixed to said first member at about the midpoint thereof for at least partly encircling the limb and for engaging said second member, said straps causing the ends of the cross-arms of said first and second members to bend to conform to the shape of the limb when tightened around the limb, thereby resisting relative movement above and below the fracture in all directions.

2. A brace according to claim 1 wherein the surfaces of said first and second members which contact the limb when said straps are tightened are provided with padding.

3. A brace according to claim 1 or 2 wherein said first member is comprised of a pair of spaced bars joined at the ends thereof, the opening between the bars allowing access to a wound without removing the brace from the limb.

4. A brace according to claim 1 wherein said second member is comprised of a pair of spaced bars joined at the ends thereof, the opening between the bars allowing access to the limb without removing the brace from the limb.

5. A brace according to claim 1 wherein the ends of the cross-arms of said first member and the ends of the cross-arm of said second member are long enough to interlap when said straps are tightened around the limb.

6. A brace according to claim 1 wherein the materials comprising the brace are radiolucent.

7. A brace according to claim 1 wherein said first and second elongate members are comprised of plastic and the flexibility of the ends of the cross-arms of said respective first and second members is achieved by molding the cross-arms of plastic which is thinner in thickness than the thickness of the plastic comprising said first and second members.

8. Apparatus for external fixation of a fracture of a long bone of a limb comprising:
   first and second substantially rigid elongate members;
   a plurality of straps affixed to said first and second elongate members, two of the straps being affixed at the respective ends of said first elongate member and one of said straps being affixed at about the midpoint of said second elongate member for encircling the limb and holding said first and second elongate members securely thereto when tightened, the straps affixed to the ends of said first elongate member adapted to be positioned above and below the fracture in the bone; and
   first and second flexible cross-arms located at each end of said first elongate member and a third cross-arm located at about the midpoint of said second elongate member, each respective cross-arm being bent by the tightening of the respective strap so as to be closely applied to the external surface of the limb, thereby cooperating with said straps to resist movement of the fractured bone above and below the fracture.

9. The apparatus of claim 8 wherein the cross-arms of said first and second elongate members are of sufficient length to interlap when said straps are tightened around the limb.

10. The apparatus of claim 8 wherein said first and second elongate members are comprised of spaced bars joined at the ends thereof to provide an opening therebetween.

11. The apparatus of claim 8 additionally comprising a layer of padding applied to said first and second elongate members.

* * * * *